United States Patent
Nakazawa et al.

(10) Patent No.: US 8,877,964 B2
(45) Date of Patent: Nov. 4, 2014

(54) CATALYST AND METHOD FOR PRODUCING ACRYLIC ACID

(75) Inventors: Yuta Nakazawa, Sanyoonoda (JP); Susumu Matsumoto, Sanyoonoda (JP); Tomoaki Kobayashi, Sanyoonoda (JP); Tatsuhiko Kurakami, Sanyoonoda (JP)

(73) Assignee: NipponKayaku KabushikiKaisha, Tokyo (JP)

( * ) Notice: Subject to any disclaimer, the term of this patent is extended or adjusted under 35 U.S.C. 154(b) by 0 days.

(21) Appl. No.: 13/882,265

(22) PCT Filed: Oct. 27, 2011

(86) PCT No.: PCT/JP2011/074855
§ 371 (c)(1),
(2), (4) Date: Apr. 29, 2013

(87) PCT Pub. No.: WO2012/060281
PCT Pub. Date: May 10, 2012

(65) Prior Publication Data
US 2013/0217915 A1  Aug. 22, 2013

(30) Foreign Application Priority Data

Nov. 1, 2010 (JP) .................................. 2010-244966

(51) Int. Cl.
| | | |
|---|---|---|
| C07C 51/235 | (2006.01) | |
| B01J 37/02 | (2006.01) | |
| C07C 51/16 | (2006.01) | |
| B01J 27/199 | (2006.01) | |
| B01J 37/00 | (2006.01) | |
| B01J 23/887 | (2006.01) | |
| B01J 23/00 | (2006.01) | |
| B01J 35/00 | (2006.01) | |
| B01J 35/04 | (2006.01) | |

(52) U.S. Cl.
CPC .............. *C07C 51/16* (2013.01); *B01J 2523/00* (2013.01); *B01J 37/0244* (2013.01); *B01J 27/199* (2013.01); *B01J 37/0045* (2013.01); *B01J 37/0036* (2013.01); *B01J 23/8877* (2013.01); *B01J 23/002* (2013.01); *C07C 51/235* (2013.01); *B01J 35/0006* (2013.01); *B01J 35/04* (2013.01)
USPC ......................................................... 562/535

(58) Field of Classification Search
CPC ................................................... C07C 51/252
See application file for complete search history.

(56) References Cited

U.S. PATENT DOCUMENTS

| | | | | |
|---|---|---|---|---|
| 5,739,392 A | * | 4/1998 | Tanimoto et al. | 562/535 |
| 6,563,000 B1 | | 5/2003 | Yunoki et al. | |
| 6,762,148 B2 | * | 7/2004 | Ohishi et al. | 502/318 |
| 2003/0060659 A1 | * | 3/2003 | Yunoki | 562/532 |
| 2003/0125580 A1 | | 7/2003 | Yunoki | |

FOREIGN PATENT DOCUMENTS

| | | |
|---|---|---|
| CN | 1328988 A | 1/2002 |
| CN | 1408700 A | 4/2003 |
| JP | 41-001775 B | 2/1966 |
| JP | 44-012129 B | 6/1969 |
| JP | 53-030688 B | 8/1978 |
| JP | 07-010802 A | 1/1995 |
| JP | 09-241209 A | 9/1997 |
| JP | 2000-336060 A | 12/2000 |
| JP | 2001-354612 A | 12/2001 |
| JP | 2003-089671 A | 3/2003 |
| JP | 2003-171340 A | 6/2003 |
| JP | 2005-120079 A | 5/2005 |

OTHER PUBLICATIONS

White et al, Basic Energy Sciences Advisory Committee Subpanel Workshop Report, Opportunities for Catalysis in the 21st Century, 2002, pp. 1-47.*
International Search Report and Written Opinion mailed Dec. 27, 2011 in corresponding PCT application No. PCT/JP2011/074855.
International Preliminary Report on Patentability issued May 14, 2013 in corresponding PCT application No. PCT/JP2011/074855.
Chinese communication, with English translation, mailed May 16, 2014 in corresponding Chinese patent application No. 201180052990.8.

* cited by examiner

*Primary Examiner* — Paul A Zucker
(74) *Attorney, Agent, or Firm* — Nields, Lemack & Frame, LLC

(57) ABSTRACT

The present invention relates to a method for producing acrylic acid through vapor-phase contact oxidation of acrolein, wherein a reactor tube is divided into at least two catalyst layers, and catalysts having a higher activity are charged in the reactor tube sequentially toward an outlet port side from a material source gas inlet port side for a reaction therein to give acrylic acid, and wherein a catalyst activity-controlling method is a method comprising: a step of mixing a molybdenum-containing compound, a vanadium-containing compound, a copper-containing compound and an antimony-containing compound with water, then drying and calcining a resulting mixture, in which a catalytically-active element composition is kept constant but material source compounds are made to vary in type to give composite metal oxides having a different activity.

4 Claims, No Drawings

US 8,877,964 B2

CATALYST AND METHOD FOR PRODUCING ACRYLIC ACID

TECHNICAL FIELD

The present invention relates to a method for producing acrylic acid through vapor-phase contact oxidation of acrolein with molecular oxygen.

BACKGROUND ART

Regarding the catalyst for producing acrylic acid through vapor-phase contact oxidation of acrolein, many composite oxide catalysts have heretofore been known as described in Patent Reference 1, Patent Reference 2, etc. Some of those catalysts have already been industrialized and used in production of acrylic acid, but the productivity thereof is not always satisfactory; and with the recent growth in demand for acrylic acid, more highly-productive catalysts have become desired.

In industrially producing acrylic acid with the catalyst, there is a demand for further increasing the productivity of acrylic acid per the catalyst unit volume and for further prolonging the catalyst life; however, when the flow rate of acrolein as material source is increased for the purpose of increasing the productivity of acrylic acid, then the reaction heat may increase and the hot spot temperature may be thereby raised owing to the accumulation of heat in the catalyst layer, therefore providing a possibility of not only resulting in yield reduction owing to excessive oxidation and in acceleration of catalyst degradation owing to thermal load but also causing runaway reaction.

Some proposals have been made for the means of depressing the temperature of hot spot areas. For example, there have been proposed a method of diluting the catalyst layer on the gas inlet port side with an inert substance (Patent Reference 3); a method of sequentially increasing the catalytically-active substance-supporting ratio (ratio by weight of active substance per catalyst) toward the gas outlet port side from the gas inlet port side (Patent Reference 4); a method of sequentially reducing the size of the catalyst toward the gas outlet port side from the gas inlet port side (Patent Reference 5); a method of lowering the catalyst activity on the gas inlet port side through addition of an alkali metal thereto (Patent Reference 6); a method of varying the catalyst ingredients and/or the amount thereof and charging the catalysts having a different activity in the system in such a manner that the activity of the catalyst could increase toward the gas outlet port side from the gas inlet port side (Patent Reference 7), etc.

BACKGROUND ART DOCUMENT

Patent Reference

[Patent Reference 1] JP-B-41-1775
[Patent Reference 2] JP-B-4442129
[Patent Reference 3] JP-B-53-30688
[Patent Reference 4] JP-A-7-10802
[Patent Reference 5] JP-A-9-241209
[Patent Reference 6] JP-A-2000-336060
[Patent Reference 7] JP-A-2003-89671

SUMMARY OF INVENTION

Problem that Invention is to Solve

Of the existing methods for depressing the temperature in hot spot areas, however, in the methods described in Patent References 1 to 5, the amount of the catalyst active substance on the gas inlet port side is smaller than that of the catalyst active substance on the gas outlet port side, and therefore, the catalyst on the gas inlet port side may degrade more rapidly than the catalyst on the gas outlet port side. As a result, the methods could attain the effect of depressing the temperature in hot spot areas in some degree, but still have a problem in that the reaction could not be continued for a long period of time while keeping a high yield in the method. In particular, in the reaction under a high load condition of using a high concentration of acrolein as material source, the problem is remarkable.

In the method of Patent Reference 6, the absolute amount of the catalyst active substance on the gas inlet port side is substantially the same as the absolute amount of the catalyst active substance on the gas outlet port side. However, the catalyst active point is reduced by addition of an alkali metal thereto, and therefore, the catalyst function that matches the amount of the catalyst active substance used could not be sufficiently performed. Accordingly, though more effective than the other methods, the method could not still solve sufficiently the problem in that the reaction could not be continued for a long period of time while keeping a high yield in the method. In addition, in the method of Patent Reference 7, when the catalysts differ in the composition thereof, then they also differ in the time-dependently varying efficacy thereof, and therefore the reaction control is difficult, and consequently, in the method, when different catalysts that extremely differ in the life thereof are combined and charged for activity control of the catalysts, the reaction balance between the catalyst layers may break down and, as the case may be, long-term continuous driving of the system would be impossible.

The present invention has an object thereof to provide a method for producing acrylic acid through vapor-phase contact oxidation of acrolein, in which any excessive accumulation of heat in the catalyst layer, as compared with that in the related art, can be prevented while keeping a high yield in the method, which solves the problem that the catalyst on the gas inlet port side worsens more rapidly than the catalyst on the gas outlet port side, and which therefore enables stable long-term use of the catalyst.

Means for Solving Problem

The present inventors have extensively studied the means for solving the above-mentioned problems and, as a result, have found that the catalyst activity can be controlled by changing the material source even though the catalyst ingredient composition is constant. Further, the inventors have found that, when at least two catalyst layers which are so controlled as to have a different catalyst activity by changing the supporting ratio thereof are prepared and when the catalysts having a higher activity are charged in a reactor tube sequentially from the material source gas inlet port side toward the outlet port side, then the hot spot temperature can be lowered more than before and the system can be driven under the condition where the catalyst activity ingredient concentration in the upper layer can be higher. On the basis of these findings, the inventors have completed the present invention.

Specifically, the invention relates to the following:

(1) A method for producing acrylic acid through vapor-phase contact oxidation of acrolein, wherein a reactor tube is divided into at least two catalyst layers, and catalysts having a higher activity are charged in the reactor tube sequentially toward an outlet port side from a material source gas inlet port side for a reaction therein to give acrylic acid, and wherein a catalyst activity-controlling method is a method comprising:

a step of mixing a molybdenum-containing compound, a vanadium-containing compound, a copper-containing compound and an antimony-containing compound with water, then drying and calcining a resulting mixture, in which a catalytically-active element composition is kept constant but material source compounds are made to vary in type to give composite metal oxides having a different activity.

(2) The method for producing acrylic acid as described in (1) above,
wherein a coated catalyst prepared by making the composite metal oxide of (1) above supported by a carrier is used as the catalyst, and
a supporting ratio of the coated catalyst is varied to control the catalyst activity.

(3) The method for producing acrylic acid as described in (1) or (2) above,
wherein a type of the antimony-containing compound is varied.

(4) The method for producing acrylic acid as described in (3) above,
wherein the antimony-containing compound is a combination of antimony trioxide and antimony acetate.

(5) The method for producing acrylic acid as described in any one of (1) to (4) above,
wherein any other metal-containing compound than the molybdenum-containing compound, the vanadium-containing compound, the copper-containing compound and the antimony-containing compound is used.

Effects Of Invention

According to the invention that provides a method for producing acrylic acid through vapor-phase contact oxidation of acrolein, any excessive accumulation of heat in the catalyst layer can be prevented, while keeping a high yield in the method, the problem in the related art that the catalyst on the gas inlet port side worsens more rapidly than the catalyst on the gas outlet port side can be solved, and the catalyst can be stably used for a long period of time for acrylic acid production.

MODE FOR CARRYING OUT INVENTION

The composite metal oxide to be used as the catalyst in the invention is not specifically defined in point of any other metal therein, so far as the oxide contains molybdenum, vanadium, copper and antimony as the catalytically-active elements therein. A preferred composition of the composite metal oxide may be represented by the following general formula:

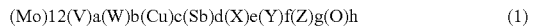
(Mo)12(V)a(W)b(Cu)c(Sb)d(X)e(Y)f(Z)g(O)h  (1)

wherein Mo, V, W, Cu, Sb and O each indicate molybdenum, vanadium, tungsten, copper, antimony and oxygen, respectively; X represents at least one element selected from an alkali metal and thallium; Y represents at least one element selected from magnesium, calcium, strontium, barium and zinc; Z represents at least one element selected from niobium, cerium, tin, chromium, manganese, iron, cobalt, samarium, germanium, titanium and arsenic; a, b, c, d, e, f, g and h each indicate the atomic ratio of the elements; relative to the molybdenum element 12, $0<a\leq10$, $0\leq b\leq10$, $0<c\leq6$, $0<d\leq10$, $0\leq e\leq0.5$, $0\leq f\leq1$, $0\leq g<6$; and h indicates the number of the oxygen atoms necessary to satisfy the atomic valences of the constitutive elements.

The catalyst for use in the invention (hereinafter this may be referred to as the catalyst in the invention) can be produced by calcining a powder, which is obtained by drying a mixture of the compounds each containing the catalytically-active element and water, optionally followed by shaping the calcined powder. The material source for the catalytically-active ingredients are not specifically defined, for which employable are any ordinary ammonium salts, nitrates, sulfates, acetates, oxides, chloride and the like that are generally used in the art. Specific examples of the compounds are as follows: The molybdenum-containing compounds include molybdenum trioxide, molybdic acid and its salts, etc.; the vanadium-containing compounds include vanadium pentoxide, vanadyl sulfate, vanadic acid and its salts, etc.; the copper-containing compounds include copper oxide, copper sulfate, copper nitrate, copper molybdate, etc.; the antimony-containing compounds include antimony trioxide, antimony pentoxide, antimony acetate, antimony trichloride, etc. The tungsten-containing compounds include tungstic acid and its salts, etc.

In the invention, the catalytically-active element composition is kept constant but the material source compounds are made to vary in type thereby controlling the activity of the catalyst. In the invention, the material source compounds may be made to vary in type for every element so that the compounds containing the same element are made to vary in type. The type of the material source compounds to be varied may be suitably determined and changed depending on the desired activity of the composite metal oxide to be obtained; but preferably, the type of the antinomy-containing compounds is varied. In this case, an especially preferred combination is composed of antimony trioxide and antimony acetate; and a catalyst prepared by using antimony acetate may have a higher activity. There may be no need to vary the type of the optional compounds containing tungsten or any other optional ingredient that are used in preparing the catalyst of the invention.

In preparing the catalyst of the invention, first, the above-mentioned, catalytically-active element-containing compounds are mixed with water to prepare an aqueous solution or aqueous dispersion. Unless otherwise specifically indicated hereinunder, the aqueous solution and the aqueous dispersion may be collectively referred to as a slurry liquid. In the invention, the slurry liquid is preferably an aqueous solution. Unless otherwise specifically indicated, the content ratio of the catalytically-active element-containing compounds in the slurry liquid preferably falls within the range of the atomic ratio of the above-mentioned formula (1). The amount of water to be used is not specifically defined so far as the entire amount of the compounds to be used could be completely dissolved in water (or uniformly mixed in water), but may be suitably determined in consideration of the drying step and the temperature in the step to be mentioned below. In general, the amount of water may be from 200 to 2000 parts by weight relative to the total weight of the compounds, 100 parts by weight. When the amount of water is too small, then the compounds could not be completely dissolved (or could not be uniformly mixed) therein. However, when the amount of water is too large, then there occur some problems in that the energy cost in the drying step may increase and the drying would be insufficient.

Next, the uniform slurry liquid obtained in the above is dried. Not specifically defined, the drying method may be any one capable of drying the slurry liquid to give a powder. For example, there may be mentioned drum drying, freeze drying, spray drying, etc. Of those, spray drying is preferred in the invention since the slurry liquid can be dried into a powder within a short period of time. The drying temperature in this case may vary depending on the concentration of the slurry liquid, the liquid feeding rate, etc.; but in general, the temperature at the outlet port of the drier may be from 85 to 130° C. Preferably, the slurry liquid is so dried that the mean particle size of the dried powder could be from 20 to 60 μm.

Next, the dry powder obtained in the above is calcined at 200 to 600° C. for 1 to 15 hours, and optionally ground to give the catalyst of the invention. Preferably, in general, the catalyst is shaped according to the shaping method mentioned below. In case where the catalyst is shaped, preferably, the calcination process is attained in two stages of pre-calcination before the shaping step and post-calcination after the shaping step. Not specifically defined, the calcination step may be attained in any known mode. The catalyst production method including the shaping method is, for example, as follows: In this case, the temperature of the pre-calcination is generally from 250 to 500° C., preferably from 300 to 450° C., and the pre-calcination time is generally from 1 to 15 hours, preferably from 3 to 6 hours. The pre-calcination step is effective for preventing the catalytically-active ingredients from powdering or peeling away while the shaped catalyst is charged in a reactor tube, and for obtaining a shaped catalyst having small abrasion degree.

The pre-calcined granules only can serve as a catalyst having a sufficient catalytic potency; however, the pre-calcined granules are preferably shaped for use herein. As the shaping method, there may be mentioned (A) a shaping method of tabletting the pre-calcined granules; (B) a shaping method of mixing the pre-calcined granules with a shaping aid such as silica gel, diatomaceous earth, alumina powder or the like, and shaping the mixture through extrusion into spherical or ring-shaped bodies; (C) a method of applying the pre-calcined granules to a spherical carrier of silicon carbide, alumina, mullite, alundum or the like having a diameter of from 2.5 to 10 mm so as to be coat-supported by the carrier, according to a tumbling granulation method or the like, etc.

As the binder for use in the above, there may be mentioned water, ethanol, polyvinyl alcohol of a polymer binder, aqueous silica sol of an inorganic binder, etc.; but preferred are alcohols, such as dials and trials, e.g., ethylene glycol, glycerin, etc.; and more preferred is glycerin. The alcohol may be used here directly as it is, but is preferably used as an aqueous solution thereof having a concentration of at least 10% by weight for the purpose of producing a high-efficacy catalyst. The amount of the binder to be used here may be generally from 10 to 50 parts by weight relative to 100 parts by weight of the pre-calcined granules.

Further optionally, a shaping aid such as silica gel, diatomaceous earth, alumina powder or the like may be used here. The amount of the shaping aid to be used may be generally from 5 to 60 parts by weight relative to 100 parts by weight of the pre-calcined granules. Still optionally, use of a strength enhancer, for example, inorganic fibers such as ceramic fibers, whiskers of the like is effective for the purpose of enhancing the mechanical strength of the catalyst. However, fibers reactive with the catalyst ingredient, such as potassium titanate whiskers or basic magnesium carbonate whiskers are unfavorable. The amount of the fibers to be used may be generally from 1 to 30 parts by weight relative to 100 parts by weight of the pre-calcined granules.

In use thereof, in general, the shaping aid and the strength enhancer may be mixed with the pre-calcined granules. On the other hand, the binder may also be mixed with the pre-calcined granules, or may be added to the shaping mold simultaneously with or before or after addition of the pre-calcined granules thereto, as described below.

Of the above-mentioned shaping methods, preferred is the tumbling granulation method (C). The method is as follows: For example, in an apparatus having a flat or surface-roughened disc at the bottom of a fixed container, the disc is rotated at a high speed so that the carrier in the container is violently stirred by repetition of the rotational movement and the orbital motion thereof, and a mixture of a binder and pre-calcined granules and optionally a shaping aid and a strength enhancer is added thereto so that the carrier is coated with the mixture. The binder may be previously mixed with the mixture, or may be added thereto simultaneously with addition of the mixture to the fixed container, or may be added thereto after the addition of the mixture, or may be added before the addition thereof; or the mixture and the binder may be suitably divided into plural portions and they may be combined in any desired manner so that the entire amount of those ingredients may be added to the container. Any of these modes may be employed here in any desired manner. Of those, in the method of dividing the mixture and the binder into plural portions, for example, it is desirable to suitably control the addition speed of the ingredients by the use of an autofeeder or the like, for the purpose of preventing the mixture from adhering to the wall of the fixed container and preventing the ingredients of the mixture from aggregating together so that the predetermined amount of the mixture could be supported by the carrier.

As specific examples of the carrier usable in the method (C), there may be mentioned spherical carriers of silicon carbide, alumina, mullite, alundum or the like having a diameter of from 2.5 to 10 mm. Of those, preferred are the carriers having a porosity of from 30 to 50% and a water absorption of from 10 to 30%. Regarding the amount of the carrier to be used, the ratio of pre-calcined granules/pre-calcined granules+carrier) may be generally from 10 to 75% by weight, preferably from 15 to 50% by weight.

The size of the shaped body of the pre-calcined granules obtained according to the above-mentioned methods (A) to (C) may be as follows: For example, when the shaped body is a columnar body, preferably, the diameter thereof is from 2 mm to 10 mm or so, and the height thereof is from 3 to 20 mm or so; and when the shaped body is a spherical body, preferably, the diameter thereof is from 3 to 15 mm or so.

Thus produced, the shaped body of the pre-calcined granules may be post-calcined to give a catalyst. In this case, the calcination temperature may be generally from 250 to 500° C., preferably from 300 to 450° C., and the calcination time may be from 1 to 50 hours.

The embodiment of the catalyst of the invention that comprises a composite metal oxide supported by a carrier as above is preferred in point of the catalyst life. Specifically, according to the related art where the catalytic activity of a supported catalyst is controlled only by controlling the supported amount of the composite metal oxide therein, in the catalyst in which the supporting ratio is small and which therefore has a low activity, the absolute amount of the composite metal oxide is small, and therefore the workload of the composite metal oxide is heavy so that the life of the catalyst is short. On the other hand, according to the present invention, the catalytic activity may be lowered by changing the type of the material source compounds to be used for the catalyst, and therefore the supporting ratio may be made relatively large so that a catalyst in which the amount of the composite metal oxide is large in the upper layer may be used and the life of the catalyst can be thereby prolonged.

In the invention, the above-mentioned, multiple catalysts each having a different activity are used. Specifically, the catalyst layer is so designed as to have multiple reaction zones, and the catalysts each having a different activity are individually arranged in these reaction zones in such a manner that the activity of the thus-arranged catalysts becomes higher toward the outlet port side from the material source gas inlet port side in the tubular axial direction of the reactor tube.

In the invention, in general, a fixed-bed multitubular reactor is used as a reactor. In the reactor of the type, the number of the reactor tubes, the catalyst-charged length, and the number of the divided zones of the catalyst layer may vary depending on the driving condition, and therefore may be suitably determined case by ease so as to attain the optimum operation results. Regarding the division of the catalyst layer, when the number of the divided zones increases, it may be easy to control the hot spot areas; but in actual fact, the catalyst layer may be divided into 2 or 3 zones to attain the intended object. The inner diameter of the reactor tube may be generally from 15 to 50 mm or so.

The production method of the invention may be an ordinary single current method or a recycle method, and may be attained under ordinary conditions. For example, a mixed gas comprising the acrolein as material source in an amount of from 2 to 10% by volume, preferably from 3 to 9% by volume, molecular oxygen in an amount of from 2 to 12% by volume, preferably from 3 to 10% by volume, water vapor in an amount of from 0 to 40% by volume, preferably from 5 to 35% by volume, an inert gas (nitrogen, carbon dioxide, etc.) in an amount of from 28 to 93% by volume, preferably from 35 to 86% by volume and the like is applied onto the above-mentioned catalyst at from 200 to 400° C. under a gauge pressure of from 0 to 200 kPaG and at a space velocity (=material source gas flow rate/apparent volume of charged catalyst) of from 500 to 3000/hr for the intended catalytic reaction. In the above-mentioned mixed gas, a vapor prepared by oxidizing propylene according to a known method may be used, and in this case, small quantities of unreacted propylene and other side products may exist in the system.

EXAMPLES

The invention is described in more detail with reference to the following Examples and Comparative Examples. Not overstepping the sprit and the scope thereof, the invention should not be limited to the following Examples. "Part" in Examples and Comparative Examples is all by weight; and the acrolein conversion and the acrylic acid yield are defined by the following formulae (1) and (2), respectively.

Acrolein Conversion (mol %)=100×(molar number of reacted acrolein)/(molar number of supplied acrolein)   (1)

Acrylic Acid Yield=100×(molar number of formed acrylic acid)/(molar number of supplied acrolein)   (2)

The molar number of the formed acrylic acid in the formula (2) is the molar number of acrylic acid formed with the catalyst of the invention.

Example 1

600 parts of deionized water at 95° C. and 16.26 parts of ammonium tungstate were put into a blending tank (A) equipped with a stirrer motor, and stirred therein. Next, 18.22 parts of ammonium metavanadate, and 110 pans of ammonium molybdate were dissolved therein. Next, 3.78 parts of antimony trioxide was added thereto. 15.56 parts of copper sulfate was dissolved in 96 parts of deionized water in a blending tank (B), and the resulting solution was added to the blending tank (A) to prepare a slurry liquid. The slurry liquid prepared in the above was dried in a spray drier in which the flow rate thereof was so controlled that the outlet port temperature could be about 100° C. In a furnace heated from room temperature at a heating rate of about 60° C./hr, the thus-obtained granules were calcined (pre-calcined) at 390° C. for about 5 hours.

Next, the pre-calcined granules were ground in a ball mill to give a powder (hereinafter this is referred to as a pre-calcined powder). While 2.4 parts of an aqueous solution of 20 wt. % glycerin was sprayed onto 36 parts of a carrier alundum having a porosity of 40%, a water absorption of 19.8% and a diameter of 4.5 mm in a tumbling granulator, 12 parts of the pre-calcined powder was processed therein so that the supporting ratio could be 25% by weight. In a furnace heated from room temperature at a heating rate of about 70° C./hr, the shaped substance was calcined at 390° C. for 5 hours to give a catalyst of the invention. The elemental ratio of the catalytically-active ingredients except oxygen of the thus-obtained catalyst of the invention was as follows:

Mo12V3W1.2Cu1.2Sb0.5   (A)

The obtained product is a catalyst A.

A catalyst B was obtained in the same manner as above, except that antimony trioxide was changed to antimony acetate so that the elemental ratio of the catalytically-active ingredients thereof could be the same as that of the above-mentioned formula (A).

A catalyst C was obtained in the same manner as that for the catalyst B, except that the supporting ratio was changed to 33% by weight.

Thus obtained, the catalysts were charged in a reactor tube having an inner diameter of 27.2 mm, into which a mixed gas prepared through vapor-phase contact oxidation of propylene with a molybdenum-bismuth catalyst followed by adding oxygen and nitrogen thereto was introduced at SV (space velocity: material source gas flow rate per unit time/apparent volume of filled catalyst) of 1800/hr for reaction.

| | |
|---|---|
| Acrolein | 5.5% by volume |
| Unreacted propylene + acrylic acid + other organic compounds | 1.9% by volume |
| Oxygen | 7.4% by volume |
| Steam | 27.0% by volume |
| Nitrogen-containing inert gas | 58.2% by volume |

The catalyst A was charged in the upper layer so as to have a charged length of 1000 mm and the catalyst C was charged in the lower layer so as to have a charged length of 2600 mm; and as a result of reaction in the reactor tube, the temperature of the heating medium for the reactor tube was 276° C., the hot spot of the catalyst layer was in the layer of the catalyst A and was at 310° C. Regarding the reaction product in this case, the acrolein conversion was 99.6% and the acrylic acid yield was 97.4%.

Comparative Example 1

The catalyst B was charged in the upper layer so as to have a charged length of 1000 mm and the catalyst C was charged in the lower layer so as to have a charged length of 2600 mm; and as a result of reaction in the reactor tube, the temperature of the heating medium for the reactor tube was 276° C., the hot spot of the catalyst layer was in the layer of the catalyst B and was at 320° C. Regarding the reaction product in this case, the acrolein conversion was 99.7% and the acrylic acid yield was 97.3%.

Comparative Example 2

The catalyst C that had been diluted with an inert substance to have a concentration of 80% by weight was charged in the upper layer so as to have a charged length of 1000 mm and the catalyst C was charged in the lower layer so as to have a charged length of 2600 mm; and as a result of reaction in the reactor tube, the temperature of the heating medium for the reactor tube was 274° C., the hot spot of the catalyst layer was in the layer of the catalyst C diluted with an inert substance, and was at 325° C. Regarding the reaction product in this case, the acrolein conversion was 99.8% and the acrylic acid yield was 97.5%.

Industrial Applicability

According to the method for producing acrylic acid of the invention, any excessive accumulation of heat in the catalyst layer can be prevented while keeping a high yield, the problem in the related art that the catalyst on the gas inlet port side worsens more rapidly than the catalyst on the gas outlet port side can be solved, and the catalyst can be stably used for a long period of time.

While the invention has been described in detail and with reference to specific embodiments thereof, it will be apparent to one skilled in the art that various changes and modifications can be made therein without departing from the spirit and scope thereof.

The present application is based on Japanese Patent Application No. 2010-244966 filed on Nov. 1, 2010, and the contents are incorporated herein by reference. Also, all the references cited herein are incorporated as a whole.

The invention claimed is:

1. A method for producing acrylic acid through vapor-phase contact oxidation of acrolein, wherein a reactor tube is divided into at least two catalyst layers, and catalysts having a higher activity are charged in the reactor tube sequentially toward an outlet port side from a material source gas inlet port side for a reaction therein to give acrylic acid, and wherein the catalyst activity-controlling method is a method comprising:

a step of mixing a molybdenum-containing compound, a vanadium-containing compound, a copper-containing compound and an antimony-containing compound with water, then drying and calcining a resulting mixture, in which a catalytically-active element composition is kept constant but material source compounds are made to vary to give composite metal oxides having a different activity, said composite metal oxides having the formula:

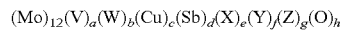

wherein Mo, V, W, Cu, Sb and O each indicate molybdenum, vanadium, tungsten, copper, antimony and oxygen, respectively; X represents at least one element selected from the group consisting of an alkali metal and thallium; Y represents at least one element selected from the group consisting of magnesium, calcium, strontium, barium and zinc; Z represents at least one element selected from the group consisting of niobium, cerium, tin, chromium, manganese, iron, cobalt, samarium, germanium, titanium and arsenic; a, b, c, d, e, f, g and h each indicate the atomic ratio of the elements; relative to the molybdenum element 12, 0<a≤10, 0≤b≤10, 0<c≤6, 0<d≤10, 0≤e≤0.5, 0≤f≤1, 0≤g<6; and h indicates the number of the oxygen atoms necessary to satisfy the atomic valences of the constitutive elements, wherein the antimony-containing compound is varied and is a combination of antimony trioxide and antimony acetate.

2. The method for producing acrylic acid as claimed in claim 1,
wherein a coated catalyst prepared by making the composite metal oxide of claim 1 supported by a carrier is used as the catalyst, and
the supporting ratio of the coated catalyst is varied to control the catalyst activity.

3. The method for producing acrylic acid as claimed in claim 1,
wherein any other metal-containing compound than the molybdenum-containing compound, the vanadium-containing compound, the copper-containing compound and the antimony-containing compound is used.

4. The method for producing acrylic acid as claimed in claim 1, wherein the reactor tube is divided into two or three catalyst layers.

* * * * *